[19] United States Patent
Lunkenheimer et al.

[11] Patent Number: 5,041,612
[45] Date of Patent: Aug. 20, 1991

[54] 1-METHYLAMINO-CYCLOPROPANE-1-CARBOXYLIC ACID DERIVATIVES

[75] Inventors: Winfried Lunkenheimer, Wuppertal; Klaus Lürssen, Gladbach, both of Fed. Rep. of Germany

[73] Assignee: Bayer Aktiengesellschaft, Leverkusen, Fed. Rep. of Germany

[21] Appl. No.: 21,292

[22] Filed: Mar. 3, 1987

Related U.S. Application Data

[63] Continuation of Ser. No. 653,375, Sep. 21, 1984, abandoned.

[30] Foreign Application Priority Data

Sep. 30, 1983 [DE] Fed. Rep. of Germany ....... 3335514

[51] Int. Cl.$^5$ .............................................. C07C 69/74

[52] U.S. Cl. ...................................... 560/124; 71/106; 71/113; 71/118; 71/121; 564/190

[58] Field of Search ...................... 560/124; 562/506; 564/190; 71/106, 113, 118, 190

[56] References Cited

FOREIGN PATENT DOCUMENTS 5782 12/1979 European Pat. Off. .............. 71/106
30287 6/1981 European Pat. Off. .

*Primary Examiner*—Michael L. Shippen
*Attorney, Agent, or Firm*—Sprung Horn Kramer & Woods

[57] ABSTRACT

New 1-methylamino-cyclopropane-1-carboxylic acid derivatives, processes for their preparation and their use as plant growth regulators are disclosed and claimed.

2 Claims, No Drawings

1-METHYLAMINO-CYCLOPROPANE-1-CARBOXYLIC ACID DERIVATIVES

This is a continuation of application Ser. No. 653,375, filed Sept. 21, 1984, now abandoned.

The invention relates to new 1-methylamino-cyclopropane-1-carboxylic acid derivatives, several processes for their preparation and their use as plant growth regulators.

It is known that 1-amino-cyclopropanecarboxylic acid which is unsubstituted at the nitrogen atom, and its hydrochloride, possess plant growth-regulating properties (see EP-OS (European Published Specification) 5,782 and EP-OS (European Published Specification) 25,141).

However, the action of these compounds is not always completely satisfactory, particularly when small amounts are used and in the case of low concentrations.

New 1-methylamino-cyclopropane-1-carboxylic acid derivatives of the general formula (I)

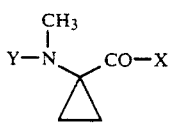

(I)

in which
X represents hydroxyl, optionally substituted alkoxy, alkenyloxy, alkinyloxy, cycloalkoxy, amino, alkylamino, dialkylamino or the radical—O⊖M⊕,
wherein
M⊕ represents one equivalent of an alkali metal or alkaline earth metal ion or an optionally substituted ammonium, sulphonium or phosphonium ion, and
Y represents hydrogen or an acyl radical, and Y cannot simultaneously represent acetyl when X represents methoxy,
and their plant-tolerated acid addition salts have now been found.

Furthermore, it has been found that the new 1-methylamino-cyclopropane-1-carboxylic acid derivatives of the general formula (I) and their plant-tolerated acid addition salts can be prepared by several processes. Thus, a) compounds of the formula (Ia)

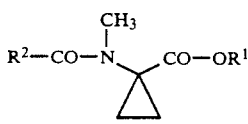

(Ia)

in which
R$^1$ represents alkyl and
R$^2$ represents hydrogen or alkyl,
are obtained by reacting 1-acylamino-cyclopropane-1-carboxylates of the formula (II)

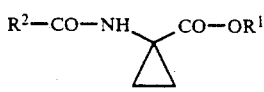

(II)

in which
R$^1$ and R$^2$ have the meaning given above,
with a methylating agent of the formula (III)

$$CH_3-Z \quad (III)$$

in which
Z represents an electron-attracting leaving group,
if appropriate in the presence of a diluent and, if appropriate, in the presence of an acid-binding agent, or b) 1-methylamino-cyclopropane-1-carboxylic acid of the formula

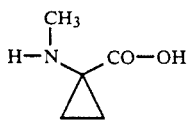

(Ib)

is obtained by reacting 1-(N-acylmethylamino)-cyclopropane-1-carboxylates of the formula (Ia)

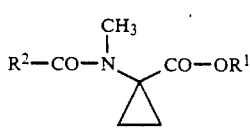

(Ia)

in which
R$^1$ and R$^2$ have the meaning given above,
with aqueous hydrochloric acid, if appropriate in the presence of a diluent, or c) compounds of the formula (Ic)

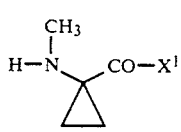

(Ic)

in which
X$^1$ represents hydroxyl, optionally substituted alkoxy, alkenyloxy, alkinyloxy, cycloalkoxy, amino, alkylamino or dialkylamino,
are obtained by reacting 1-(N-formyl-methylamino)-cyclopropane-1-carboxylic acid derivatives of the formula (Id)

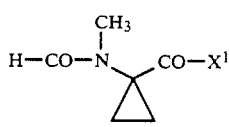

(Id)

in which
X$^1$ has the meaning given above,
with aqueous hydrochloric acid, if appropriate in the presence of a diluent, or d) compounds of the formula (Ie)

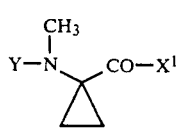

(Ie)

in which
Y and X$^1$ have the meaning given above,
are obtained by a method in which compounds of the formula (If)

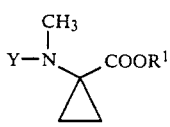 (If)

in which
Y and R¹ have the meaning given above,
α) are reacted with aqueous sodium hydroxide solution, if appropriate in the presence of a diluent, and, if required, the product is then acidified, or
β) are reacted with alcohols of the formula (IV)

R³OH   (IV)

in which
R³ represents optionally substituted alkyl, or alkenyl, alkinyl or cycloalkyl,
if appropriate in the presence of a diluent and, if appropriate, in the presence of a catalyst, or
γ) are reacted with amines of the formula (V)

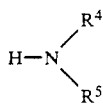 (V)

in which
R⁴ and R⁵ independently of one another represent hydrogen or alkyl,
if appropriate in the presence of a diluent, or
e) compounds of the formula (Ig)

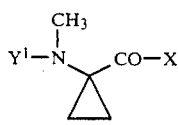 (Ig)

in which
X has the meaning given above and
Y¹ represents an acyl radical,
are obtained by reacting 1-methylamino-cyclopropane-1-carboxylic acid derivatives of the formula (Ih)

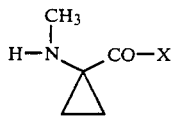 (Ih)

in which
X has the meaning given above,
with an acylating agent of the formula (VI)

Y¹-A   (VI)

in which
Y¹ has the meaning given above and
A represents an electron-attracting activating radical,
if appropriate in the presence of a diluent and, if appropriate, in the presence of an acid-binding agent and, if appropriate, in the presence of a catalyst, or
f) compounds of the formula (Ii)

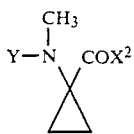 (Ii)

in which
Y has the meaning given above and
X² represents optionally substituted alkoxy, alkenoxy, alkinoxy, cycloalkoxy, amino, alkylamino, dialkylamino or the radical O⊖M⊕,
wherein
M⊕ represents one equivalent of an alkali metal or alkaline earth metal ion or an optionally substituted ammonium, sulphonium or phosphonium ion,
are obtained by reacting 1-methylamino-cyclopropane-1-carboxylic acids of the formula (Ij)

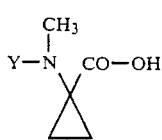 (Ij)

in which
Y has the meaning given above,
α) with alcohols of the formula (IV)

R³-OH   (IV)

in which
R³ has the meaning given above,
if appropriate in the presence of a diluent, if appropriate in the presence of an acid-binding agent and, if appropriate, in the presence of a suitable activating agent or catalyst, or
β) with amines of the formula (V)

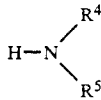 (V)

in which
R⁴ and R⁵ have the meaning given above,
if appropriate in the presence of a diluent, if appropriate in the presence of an acid-binding agent and, if appropriate, in the presence of a suitable activating agent, or
γ) with compounds of the formula (VII)

M⊕G⊖   (VII)

in which
M⊕ has the meaning given above and
G⊖ represents a suitable counter-ion,
if appropriate in the presence of a diluent and, if appropriate, in the presence of an acid-binding agent, or
g) compounds of the formula (Ik)

CH₃
|
Y—N CO—OR³ (Ik)
△ in which

Y and $R^3$ have the meaning given above,
are obtained by reacting 1-methylamino-cyclopropane-1-carboxylate salts of the formula (II)

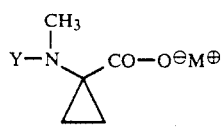 (II)

in which
Y and $M^\oplus$ have the meaning given above,
with a compound of the formula (VIII)

$R^3$-Z (VIII)

in which
$R^3$ and Z have the meaning given above,
if appropriate in the presence of a diluent.

The plant-tolerated acid addition salts of the 1-methylamino-cyclopropane-1-carboxylic acid derivatives according to the invention, of the formula (I), are obtained by subjecting the compounds obtained by processes (a) to (g) to an addition reaction with a suitable acid.

Finally, it has been found that the new 1-methylamino-cyclopropane-1-carboxylic acid derivatives of the formula (I) and their plant-tolerated acid addition salts possess plant growth-regulating properties.

Surprisingly, the new 1-methylamino-cyclopropane-1-carboxylic acid derivatives of the formula (I) and their plant-tolerated acid addition salts possess better plant growth-regulating properties than the 1-aminocyclopropane-1-carboxylic acid which is unsubstituted at the nitrogen atom, or its hydrochloride, which are similar substances chemically and in terms of their action.

Formula (I) gives a general definition of the 1-methylamino-cyclopropane-1-carboxylic acid derivatives according to the invention. In this formula,
X preferably represents hydroxyl, or straight-chain or branched alkoxy which has 1 to 18 carbon atoms and is optionally substituted by hydroxyl, halogen (in particular chlorine or bromine), amino, alkylamino having 1 to 4 carbon atoms, dialkylamino having 1 to 4 carbon atoms per alkyl group, N-acylamino (such as, for example, formylamino, acetylamino and benzoylamino), alkoxy having 1 to 4 carbon atoms, acyloxy (such as, for example, formyloxy, acetyloxy and benzoyloxy), cycloalkyl having 3 to 7 carbon atoms and/or phenyl, or represents straight-chain or branched alkenyloxy having up to 6 carbon atoms, straight-chain or branched alkinyloxy having up to 6 carbon atoms, cycloalkoxy having 3 to 7 carbon atoms, amino, alkylamino and dialkylamino, each having up to 4 carbon atoms in the straight-chain or branched alkyl radicals, or the radical —$O^\ominus M^\oplus$, wherein $M^\oplus$ preferably represents a sodium or potassium ion, one equivalent of a magnesium or calcium ion or an ammonium or mono-, di-, tri- or tetraalkylammonium ion, each having 1 to 4 carbon atoms in the individual alkyl radicals, and Y preferably represents hydrogen, formyl or a straight-chain or branched alkanoyl radical which has up to 5 carbon atoms and can be substituted by up to 9 identical or different halogen atoms; but Y cannot simultaneously represent acetyl when X represents methoxy.

Further preferred substances according to the invention are plant-tolerated acid addition salts of 1-methylamino-cyclopropane-1-carboxylic acid derivatives of the formula (I) in which X and Y have the preferred meanings given above.

Particularly preferred amongst these are those salts which are formed by addition reaction with the following acids: hydrochloric acid, hydrobromic acid, phosphoric acid, nitric acid, sulphuric acid, p-toluene-sulphonic acid and monofunctional and bifunctional carboxylic acids, such as, for example, acetic acid, maleic acid, succinic acid and fumaric acid.

Particularly preferred compounds of the formula (I) are those in which
X represents hydroxyl, methoxy, ethoxy, n- and i-propoxy, n-, i-, s- and t-butoxy, n-hexyloxy, n-octyloxy, n-dodecyloxy, 2-hydroxyethoxy, 2-bromoethoxy, 2-chloroethoxy, 2-aminoethoxy, 2-(methylamino)-ethoxy, 2-(dimethylamino)-ethoxy, 2-(formylamino)-ethoxy, 2-(acetylamino)-ethoxy, 2-methoxyethoxy, 2-ethoxyethoxy, 2-acetoxyethoxy, cyclopropylmethoxy, cyclohexylmethoxy, benzyloxy, allyloxy, propargyloxy, cyclohexyloxy, amino, methylamino, ethylamino, dimethylamino, diethylamino or the radical—$O^\ominus M^\oplus$, wherein $M^\ominus$ particularly preferably represents a sodium, potassium or ammonium ion, and
Y represents hydrogen, formyl, acetyl, propionyl, chloroacetyl, dichloroacetyl, trichloroacetyl or trifluoroacetyl,
but Y cannot simultaneously represent acetyl when X represents methoxy.

Further particularly preferred substances according to the invention are plant-tolerated acid addition salts of 1-methylamino-cyclopropane-1-carboxylic acid derivatives of the formula (I) in which X and Y have the particularly preferred meanings given above. Of special interest amongst these are those salts which are formed by addition reaction with the abovementioned acids.

In addition to the compounds mentioned in the preparation examples, the following compounds of the general formula (I) may be mentioned individually:

TABLE I

 (I)

| X | Y |
|---|---|
| $CH_3O$— | H—CO— |
| $CH_3O$— | $F_3C$—CO— |
| $C_2H_5O$— | H |
| $C_2H_5O$— | H—CO— |
| $C_2H_5O$— | $CH_3$—CO— |
| $C_2H_5O$— | $F_3C$—CO— |
| n-$C_8H_{17}$—O— | H |
| n-$C_8H_{17}$—O— | H—CO— |
| n-$C_8H_{17}$—O— | $CH_3$—CO— |
| n-$C_8H_{17}$—O— | $F_3C$—CO— |
| $C_6H_5O$— | H |
| $C_6H_5O$— | H—CO— |
| $C_6H_5O$— | $CH_3$—CO— |
| $C_6H_5O$— | $F_3C$—CO— |
| $CH_3O$—$CH_2$—O— | H |
| $CH_3O$—$CH_2$—O— | H—CO— |
| $CH_3O$—$CH_2$—O— | $CH_3$—CO— |
| $CH_3O$—$CH_2$—O— | $F_3C$—CO— |
| H—CO—NH—$CH_2$—$CH_2$—O— | H |
| H—CO—NH—$CH_2$—$CH_2$—O— | H—CO— |
| H—CO—NH—$CH_2$—$CH_2$—O— | $CH_3$—CO— |

TABLE I-continued

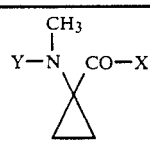

| X | Y |
|---|---|
| H—CO—NH—CH₂—CH₂—O— | F₃C—CO— |
| (CH₃)₂N—CH₂—CH₂—O— | H |
| (CH₃)₂N—CH₂—CH₂—O— | H—CO— |
| cyclopropyl-CH₂O— | CH₃—CO |
| cyclopropyl-CH₂O— | F₃C—CO— |
| cyclopropyl-CH₂O— | H |
| cyclopropyl-CH₂O— | H—CO |
| (CH₃)₂N—CH₂—CH₂—O— | CH₃—CO— |
| (CH₃)₂N—CH₂—CH₂—O— | F₃C—CO— |
| Cl—CH₂—CH₂—O— | H |
| Cl—CH₂—CH₂—O— | H—CO— |
| Cl—CH₂—CH₂—O— | CH₃—CO— |
| Cl—CH₂—CH₂—O— | F₃C—CO— |
| Br—CH₂—CH₂—O— | H |
| Br—CH₂—CH₂—O— | H—CO— |
| Br—CH₂—CH₂—O— | CH₃—CO— |
| Br—CH₂—CH₂—O— | F₃C—CO— |
| HO—CH₂—CH₂—O— | H |
| HO—CH₂—CH₂—O— | H—CO— |
| HO—CH₂—CH₂—O— | CH₃—CO— |
| HO—CH₂—CH₂—O— | F₃C—CO— |
| CH₃—CO—O—CH₂—CH₂—O— | H |
| CH₃—CO—O—CH₂—CH₂—O— | H—CO— |
| CH₃—CO—O—CH₂—CH₂—O— | CH₃—CO— |
| CH₃—CO—O—CH₂—CH₂—O— | F₃C—CO— |
| CH₂=CH—CH₂—O— | H |
| CH₂=CH—CH₂—O— | H—CO— |
| CH₂=CH—CH₂—O— | CH₃—CO— |
| CH₂=CH—CH₂—O— | F₃C—CO— |
| HC≡C—CH₂—O— | H |
| HC≡C—CH₂—O— | H—CO— |
| HC≡C—CH₂—O— | CH₃—CO— |
| HC≡C—CH₂—O— | F₃C—CO— |
| cyclohexyl-O— | H |
| cyclohexyl-O— | H—CO— |
| cyclohexyl-O— | CH₃—CO— |
| cyclohexyl-O— | F₃C—CO— |
| —NH₂ | H |
| —NH₂ | H—CO— |
| —NH₂ | CH₃—CO— |
| —NH₂ | F₃C—CO— |
| —NHCH₃ | H |
| —NHCH₃ | H—CO— |
| —NHCH₃ | CH₃—CO— |
| —NHCH₃ | F₃C—CO— |
| —N(C₂H₅)₂ | H |
| —N(C₂H₅)₂ | H—CO— |
| —N(C₂H₅)₂ | CH₃—CO— |
| —N(C₂H₅)₂ | F₃C—CO— |
| —O⁻Na⁺ | H |
| —O⁻Na⁺ | H—CO— |
| —O⁻Na⁺ | CH₃—CO— |
| —O⁻Na⁺ | F₃C—CO— |

If ethyl 1-acetylamino-cyclopropane-1-carboxylate and dimethyl sulphate are used as starting materials, the course of process (a) according to the invention can be illustrated by the following equation:

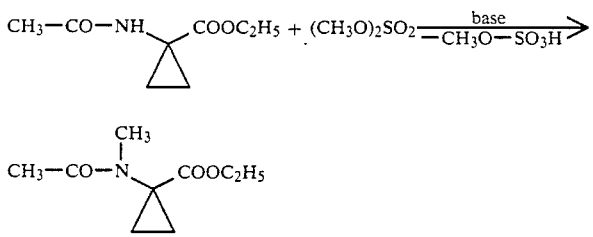

If ethyl 1-(N-acetyl-methylamino)-cyclopropane-1-carboxylate is used as starting material and concentrated aqueous hydrochloric acid is used as a reactant, the course of process (b) according to the invention can be illustrated by the following equation:

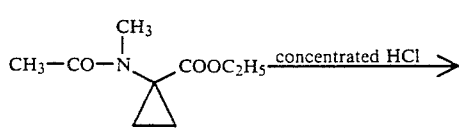

If n-octyl 1-(N-formyl-methylamino)-cyclopropane-1-carboxylate is used as a starting material and dilute aqueous hydrochloric acid is used as a reactant, the course of process (c) according to the invention can be illustrated by the following equation:

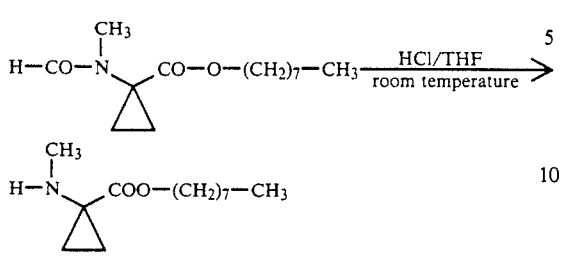

If methyl 1-(N-formyl-methylamino)-cyclopropane-1-carboxylate is used as a starting material and aqueous sodium hydroxide solution is used as a reactant, the course of process (d, variant α) according to the invention can be illustrated by the following equation:

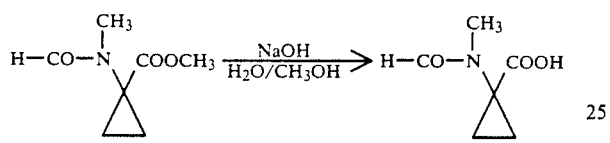

If ethyl 1-(N-acetyl-methylamino)-cyclopropane-1-carboxylate and n-octanol are used as starting materials and titanium tetra-ethylate is used as a catalyst, the course of process (d, variant β) according to the invention can be illustrated by the following equation:

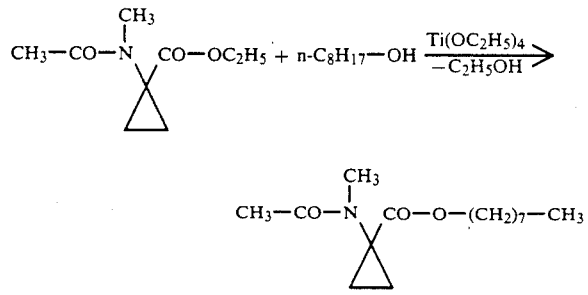

If methyl 1-methylamino-cyclopropane-1-carboxylate and methylamine are used as starting materials, the course of process (d, variant γ) according to the invention can be illustrated by the following equation:

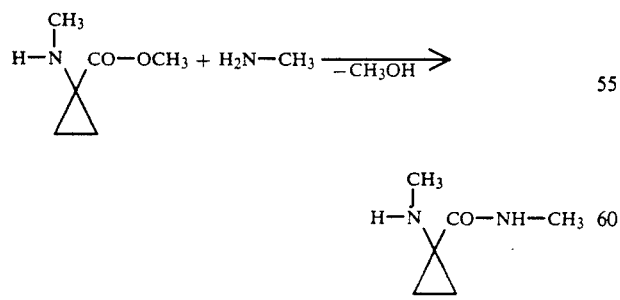

If methyl 1-methylamino-cyclopropane-1-carboxylate and ethyl formate are used as starting materials, process (e) according to the invention can be illustrated by the following equation:

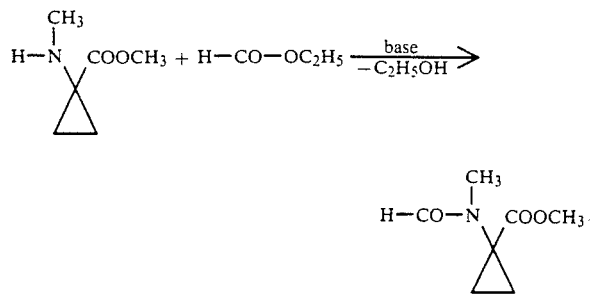

If 1-(N-acetyl-methylamino)-cyclopropane-1-carboxylic acid and 2-methoxyethanol are used as starting materials and boron trifluoride etherate is used as a catalyst, the course of process (f, variant α) according to the invention can be illustrated by the following equation:

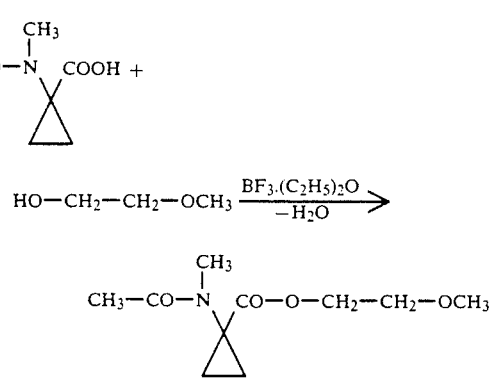

If 1-(N-formyl-methylamino)-cyclopropane-1-carboxylic acid and diethylamine are used as starting materials and N,N'-dicyclohexyl-carbodiimide is used as an activator, the course of process (f, variant β) according to the invention can be illustrated by the following equation:

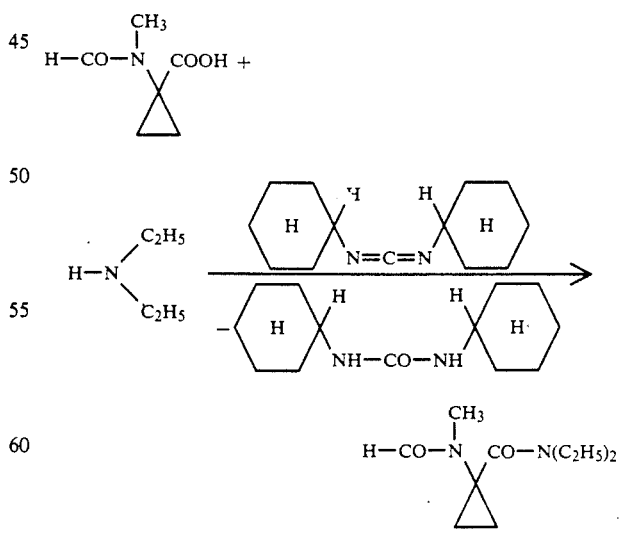

If 1-methylamino-cyclopropane-1-carboxylic acid and sodium hydroxide are used as starting materials, the course of process (f, variant γ) according to the invention can be illustrated by the following equation:

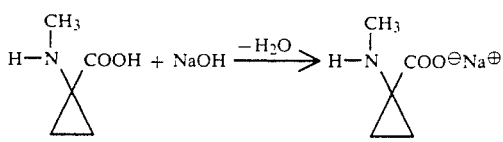

If sodium 1-methylamino-cyclopropane-1-carboxylate and benzyl chloride are used as starting materials, the course of process (g) according to the invention can be illustrated by the following equation:

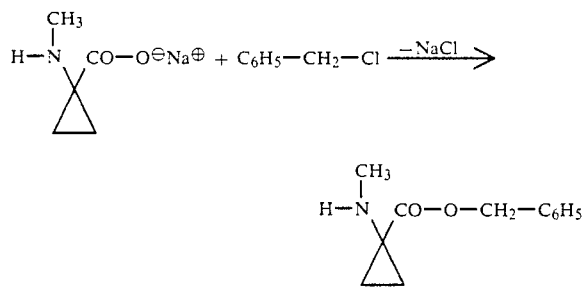

Formula (II) gives a general definition of the 1-acylamino-cyclopropane-1-carboxylic acid esters required as starting materials for carrying out process (a) according to the invention. In this formula (II), $R^1$ preferably represents methyl or ethyl, and $R^2$ preferably represents hydrogen or methyl.

The 1-acylamino-cyclopropane-1-carboxylic acid esters of the formula (II) are known (see, for example, EP-OS (European Published Specification) 5,782 and EP-OS (European Published Specification) 25,141).

Formula (III) gives a general definition of the methylating agents furthermore required as starting materials for carrying out process (a). In this formula (III), Z preferably represents halogen, in particular bromine or iodine, a methylsulphate radical, a p-toluenesulphonate radical or a mesitylenesulphonate radical.

The methylating agents of the formula (III) are generally known compounds of organic chemistry.

Formula (Ia) gives a general definition of the 1-(N-acyl-methylamino)-cyclopropane-1-carboxylic acid esters required as starting materials for carrying out process (b) according to the invention. In this formula (Ia), $R^1$ preferably represents methyl or ethyl, and $R^2$ preferably represents hydrogen or methyl.

The 1-(N-acyl-methylamino)-cyclopropane-1-carboxylic acid esters of the formula (Ia) are compounds according to the invention, and are obtainable by process (a).

Methyl 1-(N-acetyl-methylamino)-cyclopropane-1-carboxylate is an exception. This compound is known (see Nature 219, 498 [1968]).

Concentrated aqueous hydrochloric acid is preferably used as a reactant in process (b) according to the invention.

Formula (Id) gives a general definition of the 1-(N-formyl-methylamino)-cyclopropane-1-carboxylic acid derivatives required as starting materials for carrying out process (c) according to the invention. In this formula (Id), $X^1$ preferably represents hydroxyl, or straight-chain or branched alkoxy which has 1 to 18 carbon atoms and is optionally substituted by hydroxyl, halogen (in particular chlorine or bromine), amino, alkylamino having 1 to 4 carbon atoms, dialkylamino having 1 to 4 carbon atoms per alkyl group, N-acylamino (such as, for example, formylamino, acetylamino and benzoylamino), alkoxy having 1 to 4 carbon atoms, acyloxy (such as, for example, formyloxy, acetyloxy and benzoyloxy), cycloalkyl having 3 to 7 carbon atoms and/or phenyl, or represents straight-chain or branched alkenyloxy having up to 6 carbon atoms, straight-chain or branched alkinyloxy having up to 6 carbon atoms, cycloalkoxy having 3 to 7 carbon atoms, amino, alkylamino and dialkylamino, each having up to 4 carbon atoms in the straight-chain or branched alkyl radicals.

Particularly preferred starting materials for process (c) according to the invention are compounds of the formula (Id) in which $X^1$ represents hydroxyl, methoxy, ethoxy, n- and i-propoxy, n-, i- and s-butoxy, n-hexyloxy, n-octyloxy, n-dodecyloxy, 2-hydroxyethoxy, 2-bromoethoxy, 2-chloroethoxy, 2-aminoethoxy, 2-(methylamino)-ethoxy, 2-(dimethylamino)-ethoxy, 2-(formylamino)-ethoxy, 2-(acetylamino)-ethoxy, 2-methoxyethoxy, 2-ethoxyethoxy, 2-acetoxy-ethoxy, cyclopropylmethoxy, cyclohexylmethoxy, benzyloxy, allyloxy, propargyloxy, cyclohexyloxy, amino, methylamino, ethylamino, dimethylamino and diethylamino.

The 1-(N-formyl-methylamino)-cyclopropane-1-carboxylic acid derivatives of the formula (Id) were hitherto unknown. However, they can be prepared in a simple manner by a number of the abovementioned processes according to the invention.

Formula (If) gives a general definition of the 1-methylamino-cyclopropane-1-carboxylic acid esters required as starting materials in carrying out process (d) according to the invention. In this formula (If), $R^1$ preferably represents methyl or ethyl; Y preferably has those meanings which have already been mentioned in the description of the substances according to the invention, of the formula (I), as being preferred for this radical.

The 1-methylamino-cyclopropane-1-carboxylic acid esters of the formula (If) were hitherto unknown. However, they can be prepared in a simple manner by abovementioned processes according to the invention.

Aqueous sodium hydroxide solution is used as a reactant in carrying out process (d, variant α) according to the invention.

Formula (IV) gives a general definition of the alcohols furthermore required as starting materials in carrying out process (d, variant β) according to the invention. In this formula, $R^3$ preferably represents straight-chain or branched alkyl which has 1 to 18 carbon atoms and is optionally substituted by hydroxyl, halogen (such as, for example, chlorine and bromine), amino, alkylamino having 1 to 4 carbon atoms, dialkylamino having 1 to 4 carbon atoms per alkyl group, acylamino (such as, for example, formylamino, acetylamino and benzoylamino), alkoxy having 1 to 4 carbon atoms, acyloxy (such as, for example, formyloxy, acetyloxy and benzoloxy), cycloalkyl having 3 to 7 carbon atoms and/or phenyl, or represents straight-chain or branched alkenyl having up to 6 carbon atoms, straight-chain or branched alkinyl having up to 6 carbon atoms and cycloalkyl having 3 to 7 carbon atoms.

Particularly preferred starting materials for carrying out process (d, variant β) according to the invention are alcohols of the formula (IV) in which $R^3$ represents methyl, ethyl, n- and i-propyl, n-, i-, s- and t-butyl, n-hexyl, n-octyl, n-dodecyl, 2-hydroxyethyl, 2-bromoethyl, 2-chloroethyl, 2-(dimethylamino)-ethyl, 2-(formylamino)-ethyl, 2-(acetylamino)-ethyl, 2-methoxyethyl, 2-ethoxyethyl, 2-acetoxyethyl, cyclopropylmethyl, cyclohexylmethyl, benzyl, allyl, propargyl or cyclohexyl.

The alcohols of the formula (IV) are generally known compounds of organic chemistry.

Formula (V) gives a general definition of the amines furthermore required as starting materials for carrying out process (d, variant γ) according to the invention.

In this formula (V), $R^4$ and $R^5$ independently of one another preferably represent hydrogen or straight-chain or branched alkyl having up to 4 carbon atoms, in particular hydrogen, methyl and ethyl. The amines of the formula (V) are generally known compounds of organic chemistry.

Formula (Ih) gives a general definition of the 1-methylamino-cyclopropane-1-carboxylic acid derivatives required as starting materials for carrying out process (e) according to the invention. In this formula (Ih), X preferably has those meanings which have already been mentioned in the description of the substances according to the invention, of the formula (I), as being preferred for this radical.

The 1-methylamino-cyclopropane-1-carboxylic acid derivatives of the formula (Ih) were hitherto unknown. However, they can be prepared in a simple manner by a number of the abovementioned processes according to the invention.

Formula (VI) gives a general definition of the acylating agents furthermore required as starting materials for carrying out process (e) according to the invention. In this formula (VI), $Y^1$ preferably represents formyl, or alkanoyl which has 1 to 4 carbon atoms in the straight-chain or branched alkyl part and can be substituted by up to 9 identical or different halogen atoms. A preferably represents one of the customarily used radicals which activate acyl groups, such as, for example, halogen, in particular chlorine or bromine, or represents active ester radicals, such as, for example, optionally substituted alkoxy groups, anhydride radicals, such as, for example, optionally substituted acyloxy groups, or represents the N,N'-dicyclohexylcarbodiimide adduct radical of the formula

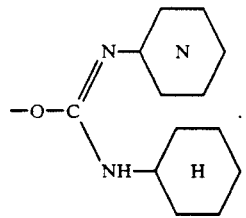

Particularly preferred starting materials for carrying out process (e) according to the invention are acylating agents of the formula (VI) in which $Y^1$ represents formyl, acetyl, propionyl, chloroacetyl, dichloroacetyl, trichloroacetyl or trifluoroacetyl, and A has the meanings mentioned above as being preferred.

The acylating agents of the formula (VI) are generally known compounds of organic chemistry.

Formula (Ij) gives a general definition of the 1-methylamino-cyclopropane-1-carboxylic acids required as starting materials for carrying out process (f) according to the invention. In this formula (Ij), Y preferably has those meanings which have already been mentioned in the description of the substances according to the invention, of the formula (I), as being preferred for this radical.

The 1-methylamino-cyclopropane-1-carboxylic acids of the formula (Ij) were hitherto unknown. However, they can be prepared in a simple manner by a number of the abovementioned processes according to the invention.

The alcohols of the formula (IV) which are furthermore required as starting materials in carrying out process (f, variant α) according to the invention have already been discussed in detail in connection with the description of process (d, variant β) according to the invention.

The amines of the formula (V) which are furthermore required as starting materials in carrying out process (f, variant β) according to the invention have already been discussed in detail in connection with the description of process (d, variant γ) according to the invention.

Formula (VII) gives a general definition of the compounds required as reactants in carrying out process (f, variant γ) according to the invention. In this formula (VII), $M^\oplus$ preferably represents a sodium or potassium ion, a magnesium or calcium ion or an ammonium or mono-, di-, tri- or tetraalkylammonium ion, each of which have up to 4 carbon atoms in the individual alkyl radicals. $G^\ominus$ preferably represents one equivalent of a halide, oxide, hydroxide or carbonate or bicarbonate ion.

The salts of the formula (VII) are generally known compounds.

Formula (II) gives a general definition of the 1-methylamino-cyclopropane-1-carboxylate salts required as starting materials for carrying out process (g) according to the invention. In this formula (II), Y and $M^\oplus$ preferably have those meanings which have already been mentioned in the description of the substances according to the invention, of the formula (I), as being preferred for these radicals.

The 1-methylamino-cyclopropane-1-carboxylate salts of the formula (II) were hitherto unknown. However, they can be prepared in a simple manner by the abovementioned process (f, variant γ) according to the invention.

Formula (VIII) gives a general definition of the compounds furthermore required as starting materials for carrying out process (g) according to the invention. In this formula (VIII), $R^3$ preferably has those meanings which have already been mentioned in the description of the alcohols of the formula (IV) as being preferred for this radical. Z preferably has those meanings which have already been mentioned in the description of the methylating agents of the formula (III) as being preferred for this radical.

The compounds of the formula (VIII) are generally known compounds of organic chemistry.

Suitable diluents for process (a) according to the invention are inert organic solvents. These preferably include aliphatic or aromatic hydrocarbons, such as, for example, benzine, benzene, toluene, xylene, pentane, hexane, esters, such as ethyl acetate, ethers, such as tetrahydrofuran, dioxane or dimethoxyethane, or dipolar aprotic solvents, such as acetonitrile, propionitrile, dimethylformamide, dimethyl sulphoxide or hexamethylphosphoric acid triamide.

Suitable acid-binding agents for process (a) according to the invention are all customary organic and, in particular, inorganic bases. Alkali metal hydroxides, hydrides or carbonates, such as, for example, sodium hydride, sodium hydroxide or potassium hydroxide or sodium carbonate or potassium carbonate, are particularly preferably used.

In carrying out process (a) according to the invention, the reaction temperatures can be varied within a substantial range. In general, the reaction is carried out at between 0° C. and 150° C., preferably between 20° C. and 120° C.

In carrying out process (a) according to the invention, in general 1 to 10 mol, preferably 1 to 5 mol, of the methylating agent of the formula (III) are employed per mol of the 1-acylamino-cyclopropane-1-carboxylic acid ester of the formula (II). In a particular embodiment, the preparation of the starting compounds of the formula (II) can be carried out in accordance with EP-OS (European Published Specification) 25,141, and the subsequent reaction can be carried out by process (a) according to the invention, in a "one-pot reaction", without isolation of the intermediates of the formula (II) (see preparation examples). The substances according to the invention, of the formula (Ia), are worked up and isolated by generally customary methods.

Suitable diluents for carrying out process (b) according to the invention are aqueous or water-miscible organic solvents. An excess of concentrated aqueous hydrochloric acid is preferably used as the diluent.

In process (b) according to the invention, the reaction temperatures can be varied within a substantial range. In general, the reaction is carried out at between 50° C. and 120° C., preferably at the reflux temperature.

For carrying out process (b) according to the invention, 1 to 30 mol of concentrated aqueous hydrochloric acid are employed per mol of the 1-(N-acylmethylamino)cyclopropane-1-carboxylic acid ester of the formula (Ia), and the reaction mixture is heated under reflux for several hours. For working up, the reaction mixture is evaporated down in vacuo, and the volatile by-products of the reaction are thus removed. The 1-(N-methylamino)cyclopropanecarboxylic acid of the formula (Ib) remains behind in the form of its hydrochloride, as a crystalline solid which can be converted to the free acid of the formula (Ib) by customary processes (for example, with propylene oxide) (see, for example, EP-OS (European Published Specification) 25,141).

Suitable diluents for process (c) according to the invention are water or water-miscible organic diluents. Mixtures of aqueous hydrochloric acid with suitable organic diluents, such as, for example, methanol, ethanol, tetrahydrofuran, dioxane or acetonitrile, are preferably used.

In process (c) according to the invention, the reaction temperatures can be varied within a substantial range. In general, the reaction is carried out at between −20° C. and +50° C., preferably at room temperature.

For carrying out process (c) according to the invention, in general 1 to 2 mol, preferably an equimolar amount, of aqueous hydrochloric acid is employed per mol of the 1-(N-formyl-methylamino)-cyclopropane-1-carboxylic acid derivative of the formula (Id), and the reaction mixture is stirred for several hours at the temperature required in each case.

For working up, the reaction mixture is evaporated down in vacuo, and the diluent and other volatile components are thus removed. The 1-methylamino-cyclopropane-1-carboxylic acid derivatives of the formula (Ic) remain behind as hydrochlorides, in solid form, and can be converted to the substances of the formula (Ic) by customary methods (for example, with propylene oxide) (see, for example, EP-OS (European Published Specification) 25,141).

Suitable diluents for process (d, variant α) according to the invention are likewise water or water-miscible organic solvents. Water or alcohol/water mixtures are preferably used, methanol or ethanol being particularly preferred as the alcohol component.

In process (d, variant α) according to the invention, the reaction temperatures can be varied within a substantial range. In general, the reaction is carried out at between 0° C. and 100° C., preferably between 20° C. and 80° C.

For carrying out process (d, variant α) according to the invention, in general 1 to 2 mol, preferably 1 to 1.5 mol, of aqueous sodium hydroxide solution are employed per mol of the 1-methylamino-cyclopropane-1-carboxylic acid ester of the formula (If). In a preferred embodiment, a suitable pH value in the basic range is maintained while the aqueous sodium hydroxide solution is metered in at the rate at which it reacts with the ester, so that an excessively alkaline reaction medium is avoided. When the reaction is complete, the free 1-methylamino-cyclopropane-1-carboxylic acids of the formula (Ie) are obtained by neutralization and evaporation of the solvent.

Suitable diluents for process (d, variant β) according to the invention are likewise inert organic solvents. Ethers, such as, for example, dioxane or tetrahydrofuran, are preferably used. However, it is also possible for the alcohol of the formula (IV) which is employed as a reactant to be used, in an appropriate excess, as the diluent.

Particularly suitable catalysts for process (d, variant β) according to the invention are acidic catalysts. Lewis acids, such as, for example, boron trifluoride, or titanium tetralkylates, such as, for example, titanium tetracethylate or titanium tetraisopropylate, are particularly advantageously used. It is also possible to use inorganic zeolites which bind the low molecular alcohol liberated and hence remove it from the reaction equilibrium.

In process (d, variant β) according to the invention, the reaction temperatures can be varied within a substantial range. In general, the reaction is carried out at between 0° C. and 120° C., preferably between 30° C. and 100° C.

For carrying out process (d, variant β) according to the invention, 1 to 30 mol of the alcohol of the formula (IV) and 0.1 to 2 mol of the catalyst are employed per mol of the 1-methylamino-cyclopropane-1-carboxylic acid ester of the formula (If). Working up and isolation of the reaction products are carried out by generally customary methods.

Suitable diluents for process (d, variant γ) according to the invention are likewise inert organic solvents. Protic solvents, in particular alcohols, such as methanol, ethanol or isopropanol, are preferably used.

In process (d, variant γ) according to the invention, the reaction temperatures can be varied within a substantial range. In general, the reaction is carried out at between −10° C. and +120° C., preferably between +10° C. and +80° C.

For carrying out process (d, variant γ) according to the invention, 1 to 10 mol of the amine of the formula (V) are employed per mol of the 1-methylamino-cyclopropane-1-carboxylic acid ester of the formula (If).

Working up and isolation of the reaction products are carried out by generally customary methods.

Particularly suitable diluents for process (e) according to the invention are inert organic solvents. Preferably used compounds are aliphatic or aromatic, optionally halogenated hydrocarbons, such as benzine, benzene, toluene, xylene, pentane, hexane, heptane, cyclohexane, petroleum ether, ligroin, methylene chloride, ethylene chloride, chloroform, carbon tetrachloride, chlorobenzene or dichlorobenzene, ethers, such as diethyl ether or diisopropyl ether, ethylene glycol dimethyl ether, tetrahydrofuran or dioxane, ketones, such as acetone or butanone, methyl isopropyl ketone or methyl isobutyl ketone, esters, such as ethyl acetate, nitriles, such as acetonitrile or propionitrile, amides, such as dimethylformamide, dimethylacetamide, N-methylpyrrolidone or hexamethylphosphoric acid triamide.

If acylating agents of the formula (VI) are used in liquid form, it is also possible to employ these, in an appropriate excess, as diluents.

Suitable acid-binding agents for process (e) according to the invention are all inorganic and organic bases which can customarily be used. Preferably used compounds are alkali metal hydroxides or alkali metal carbonates, such as, for example, sodium hydroxide, potassium hydroxide, sodium carbonate or potassium carbonate, or tertiary amines, such as, for example, triethylamine, N,N-dimethylaniline, pyridine, 4-(N,N-dimethylamino)pyridine, diazabicyclooctane (DABCO), diazabicyclononene (DBN) or diazabicycloundecene (DBU).

In process (e) according to the invention, the reaction temperatures can be varied within a substantial range. In general, the reaction is carried out at between $-20°$ C. and $+150°$ C., preferably between $0°$ C. and $+100°$ C.

For carrying out process (e) according to the invention, in general 1 to 30 mol, preferably 1 to 10 mol, of the acylating agent of the formula (VI) and 1 to 3 mol, preferably 1 to 2 mol, of the acid-binding agent are employed per mol of the 1-methylamino-cyclopropane-1-carboxylic acid derivative of the formula (Ih). Working up and isolation of the reaction products are carried out by generally customary processes.

Suitable diluents for process (f, variant α) according to the invention are likewise inert organic solvents. The solvents mentioned in the case of process (e) are preferably used. However, it is also possible for the alcohol of the formula (IV) which is used as a reactant to be employed, in an appropriate excess, as the diluent.

In process (f, variant α) according to the invention, all customary acid acceptors can be used as the acid-binding agents. Preferably used compounds are tertiary aliphatic, aromatic and heterocyclic amines, such as, for example, triethylamine, N,N-dimethylaniline, N,N-dimethylbenzylamine, pyridine, 4-dimethylaminopyridine, diazabicyclooctane (DABCO), diazabicyclononene (DBN) or diazabicycloundecene (DBU).

All activating agents or catalysts which are customarily used for esterifications can be employed as activating agents or catalysts for process (f, variant α) according to the invention. These include protic acids, such as, for example, sulphuric acid or p-toluenesulphonic acid, Lewis acids, such as, for example, boron trifluoride, condensing agents, such as, for example, N,N'-dicyclohexylcarbodiimide (DCC) or 2-ethoxy-N-ethoxycarbonyl-1,2-dihydroquinoline (EEDQ), acyl halide formers, such as, for example, phosphorus pentachloride, phosphorus tribromide or thionyl chloride, or anhydride formers, such as, for example, ethyl chloroformate or 4-nitrophenyl chloro-formate.

In process (f, variant α) according to the invention, the reaction temperatures can be varied within a substantial range. In general, the reaction is carried out at between $-20°$ C. and $+150°$ C., preferably between $0°$ C. and $+120°$ C.

For carrying out process (f, variant α) according to the invention, in general 1 to 30 mol, preferably 1 to 10 mol, of the alcohol of the formula (IV), 0.1 to 2 mol of the activating agent or catalyst and 1 to 2 mol of the acid-binding agent are employed per mol of the 1-methylamino-cyclopropane-1-carboxylic acid of the formula (I). Working up and isolation of the reaction products are carried out by generally customary processes. In a preferred embodiment, it is also possible first to prepare an activated complex of acid and activating agent from the 1-methylamino-cyclopropane-1-carboxylic acid of the formula (Ij) and the activating agent, in an initial reaction, if appropriate in the presence of the acid-binding agent, and to isolate this complex, and, in a 2nd stage, to react this complex, in a separate reaction, with the alcohol of the formula (IV), if appropriate in the presence of the acid-binding agent.

In this case too, the process, the working-up and the isolation of the particular end products are carried out by generally customary methods (see, for example, E. K. Euranto in S. Patai "The Chemistry of Carboxylic Acids and Esters", Interscience Publishers, London 1969, page 505 et seq.).

Suitable diluents for process (f, variant β) according to the invention are likewise inert organic solvents. The solvents mentioned in the case of process (e) are preferably used.

In process (f, variant β) according to the invention, suitable acid-binding agents are likewise all customary acid-binding agents. The inorganic bases are tertiary amines listed in the case of processes (e) and (f, variant α) are preferably used. However, it is also possible to use, as the acid-binding agent, an appropriate excess of the amine of the formula (VI) which is employed as a reactant.

All activating agents customarily used in amidation reactions can be employed as activating agents for process (f, variant β) according to the invention. Acyl halide formers, such as phosphorus tribromide, phosphorus pentachloride, phosphorus oxychloride or thionyl chloride, anhydride formers, such as ethyl chloroformate, and condensing agents, such as N,N'-dicyclohexylcarbodiimide (DCC), 2-ethoxy-N-ethoxycarbonyl-1,2-dihydroquinoline (EEDQ) or triphenylphosphine/carbon tetrachloride, may be mentioned as examples.

In process (f, variant β) according to the invention, the reaction temperatures can be varied within a substantial range. In general, the reaction is carried out at between $-20°$ C. and $+220°$ C., preferably between $0°$ C. and $+150°$ C.

For carrying out process (f, variant β) according to the invention, in general 1 to 5 mol, preferably 1 to 3 mol, of the amine of the formula (V) and 1 to 2 mol of the acid-binding agent and 1 to 2 mol of the activating agent are employed per mol of the 1-methylamino-cyclopropane-1-carboxylic acid of the formula (Ij). Working up and isolation of the reaction products are carried out by generally customary processes. As in the case of the procedure of process (f, variant α) according to the invention, it is also possible in this case, in a particular embodiment, first to prepare an activated complex of acid and activating agent from the 1-methylamino-cyclopropane-1-carboxylic acid of the formula (Ij) and the activating agent, in an initial reaction, if appropriate in the presence of the acid-binding agent, and to isolate this complex, and, in a 2nd stage, to react this complex, in a separate reaction, with the amine of the formula (V), if appropriate in the presence of the acid-binding agent. In this case too, the process, the working-up and the isolation of the particular end products are carried out by generally customary methods.

Particularly suitable diluents for carrying out process (f, variant γ) according to the invention are polar organic solvents or water. Alcohols, such as, for example, methanol or ethanol, or alcohol/water mixtures are preferably used.

In carrying out process (f, variant γ) according to the invention, the reaction temperatures can be varied within a substantial range. In general, the reaction is carried out at between $-20°$ C. and $+100°$ C., preferably between $0°$ C. and $+80°$ C.

For carrying out process (f, variant γ) according to the invention, in general 1 to 3 mol, preferably equimolar amounts, of the salt of the formula (VII) are employed per mol of the 1-methylamino-cyclopropane-1-carboxylic acid of the formula (Ij). Isolation of the reaction products is carried out in general by distilling off the diluent.

Suitable diluents for carrying out process (g) according to the invention are likewise organic solvents. The hydrocarbons or dipolar aprotic solvents listed for process (a) are preferably used.

In carrying out process (g) according to the invention, the reaction temperatures can likewise be varied within a substantial range. In general, the reaction is carried out at between $20°$ C. and $180°$ C., preferably between $50°$ C. and $120°$ C.

For carrying out process (g) according to the invention, in general 1 to 10 mol, preferably 1 to 3 mol, of the alkylating agent of the formula (VIII) are employed per mol of the 1-methylamino-cyclopropane-1-carboxylate salt of the formula (Ie). Working up and isolation of the reaction products are carried out by generally customary methods.

The following acids are preferably used for the preparation of plant-tolerated acid addition salts of the compounds of the general formula (I): hydrohalic acids, such as, for example, hydrochloric acid and hydrobromic acid, in particular hydrochloric acid, or phosphoric acid, nitric acid, sulphuric acid, monofunctional and bifunctional carboxylic acids and hydroxycarboxylic acids, such as, for example, acetic acid, maleic acid, succinic acid or fumaric acid, and sulphonic acids, such as, for example, p-toluenesulphonic acid and naphthalene-1,5-disulphonic acid.

The acid addition salts of the compounds of the general formula (I) can be obtained in a simple manner by customary salt formation methods, for example by dissolving a compound of the general formula (I) in a suitable organic solvent and adding the acid, for example hydrochloric acid, and can be isolated in a known manner, for example by filtration, and, if required, purified by washing with an inert organic solvent.

The active compounds according to the invention engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

Plant growth-regulating compounds can be employed, for example, to inhibit vegetative growth of the plants. Such inhibition of growth is inter alia of economic interest in the case of grasses, since it is thereby possible to reduce the frequency of cutting the grass in ornamental gardens, parks and sportsgrounds, at verges, at airports or in fruit orchards. The inhibition of growth of herbaceous and woody plants at verges and in the vicinity of pipelines or overland lines or, quite generally, in areas in which heavy additional growth of plants is undesired, is also of importance.

The use of growth regulators to inhibit the growth in length of cereals is also important. The danger of lodging of the plants before harvesting is thereby reduced or completely eliminated. Furthermore, growth regulators can strengthen the stem of cereals, which again counteracts lodging. Use of growth regulators for shortening and strengthening the stem enables higher amounts of fertiliser to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beet, sugar cane, pineapples and citrus fruit or to increase the protein content in soya or cereals. Using growth regulators it is also possible, for example, to inhibit the degradation of desired constituents, such as, for example, sugar in sugar beet or sugar cane, before or after harvesting. It is also possible favourably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree (thinning out) in order to interrupt the alternance. By alternance there is understood the peculiarity of some varieties of fruit to produce very different yields from year to year, for endogenic reasons. Finally, using growth regulators it is possible to reduce the force required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants, such as, for example, pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants to frost, drought or a high salt content in the soil can be induced with growth regulators. Cultivation of plants in regions which are usually unsuitable for this purpose thereby becomes possible.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surfaceactive agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example, ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, maize cobs asnd tobacco stalks. As emulsifying and/or foam-forming agents there are suitable: for example, non-ionic and anionic emulsifiers, such as polyoxyethylene-fatty acid esters, polyoxyethylene-fatty alcohol ethers, for example alkylaryl polyglycol ethers, alkylsulphonates, alkyl-sulphates, arylsulphonates as well as albumin hydrolysation products. As dispersing agents there are suitable: for example, ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, and also as mixtures with fertilisers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomising, scattering, dusting, foaming, coating and the like. Furthermore, it is possible to apply the active compounds in accordance with the ultra-low volume process or to inject the active compound preparation or the active compound itself into the soil. It is also possible to treat the seeds of plants.

The amounts applied can be varied within a substantial range. In general, 0.01 to 50 kg, preferably 0.05 to 10 kg, of the active compound are employed per hectare of soil surface.

As regards the time of application, the rule is that the growth regulators are applied within a preferred period of time, the exact definition of which depends on the climatic and vegetative circumstances.

The preparation and the use of the active compounds according to the invention can be seen from the examples which follow.

PREPARATION EXAMPLES

EXAMPLE 1

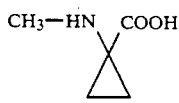

Process b

A mixture of 2.5 g (0.0146 mol) of methyl 1-(N-acetyl-methylamino)-cyclopropane-1-carboxylate and 15 ml of concentrated hydrochloric acid was heated under reflux for 5 hours. The reaction solution was evaporated down in vacuo, the residue was dissolved in 2.9 ml of methanol, and 1.7 g (0.0292 mol) of propylene oxide were added dropwise at 10° C. to 20° C., while stirring. Stirring was continued for one hour at 20° C., and the reaction mixture was then kept at 0° C. for 15 hours. The precipitate which separated out was filtered off under suction, and dried at 40° C.

1.2 g (71.4% of theory) of 1-methylamino-cyclopropane-1-carboxylic acid of melting point 237° C. to 238° C. (decomposition) were obtained in this manner.

Preparation of the starting material

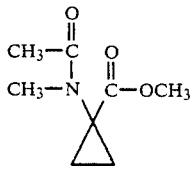

13.9 g (0.11 mol) of dimethyl sulphate were added dropwise to a melt of 17.3 g (0.1 mol) of methyl N-acetylmethionine at 110° C. in the course of 20 minutes, and stirring was continued for a further 3 hours at 110° C.

The reaction mixture obtained was dissolved in 70 ml of dimethylformamide, 55.3 g (0.4 mol) of potassium carbonate were added, and thereafter 21.3 g (0.15 mol) of methyl iodide were added dropwise at 100° C. —Stirring was continued for a further 3 hours at 100° C. and the mixture was then cooled, after which it was diluted with methylene chloride, filtered over kieselguhr and evaporated down in vacuo, the residue was dissolved in acetonitrile, the solution was treated with active carbon and filtered, and the solvent was removed in vacuo.

19.2 g (100% of theory) of methyl 1-(N-acetylmethylamino)-cyclopropane-1-carboxylate were obtained in this manner, and this product was processed further without purification.

EXAMPLE 2

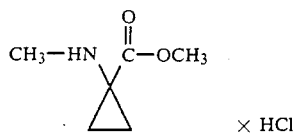

Process f, variant α

86.5 g (1.2 mol) of thionyl chloride were added dropwise to 300 ml of methanol at −10° C., and thereafter 36.9 g (0.32 mol) of 1-methylamino-cyclopropane-1-carboxylic acid were introduced in portions. Stirring was carried out for 5 hours at room temperature, and the mixture was allowed to stand overnight. The mixture was worked up by filtering it, evaporating down the filtrate in vacuo and heating the residue together with 7 g of active carbon for 10 minutes in methanol. After filtration and evaporation, 45.9 g (86.6% of theory) of methyl 1-methylamino-cyclopropane-1-carboxylate hydrochloride were obtained as a yellowish viscous oil of refractive index $n_D^{23.5}$: 1.4798.

EXAMPLE 3

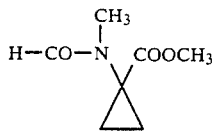

Process e 2.5 g (0.024 mol) of triethylamine were added dropwise to a mixture of 3 g (0.018 mol) of methyl 1-methylamino-cyclopropane-1-carboxylate hydrochloride and 36 ml of ethyl formate, under reflux. When the addition was complete, the mixture was boiled under reflux for a further 50 hours and cooled, after which the precipitated product was filtered off under suction and the volatile components were removed in vacuo.

In this manner, 2.8 g (99% of theory) of methyl 1-(N-formyl-methylamino)-cyclopropane-1-carboxylate were obtained in the form of an oil.

IR (CHCl$_3$): $\nu_{co}$=1679 and 1733 cm$^{-1}$.

EXAMPLE 4

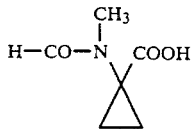

Process d, variant α

A solution of 36.2 g (0.23 mol) of methyl 1-(N-formyl-methylamino)-cyclopropane-1-carboxylate in 230 ml of methanol was titrated with aqueous 2N sodium hydroxide solution against phenolphthalein as indicator, the titration being carried out for 2 hours at room temperature and then for 2 hours at 70° C. When the reaction was complete, the cooled solution was brought to pH 4 by the addition of a strongly acidic ion exchanger (Lewatit S 100, H⊕ form), and was then filtered, and evaporated down in vacuo. The crystalline residue was stirred with ethanol, filtered off under suction and dried.

In this manner, 21.2 g (64.4% of theory) of 1-(N-formyl-methylamino)-cyclopropane-1-carboxylic acid of melting point 210° C. were obtained. The compounds of the formula (I), listed in Table 2 below, were obtained according to the methods described before.

TABLE 2

$$\triangleright\!\!<\!\!\begin{array}{c}\text{CH}_3\\|\\ \text{N}-\text{Y}\\ \text{CO}-\text{X}\end{array} \quad (\text{I})$$

| Example No. | Y | X | Physical constants |
|---|---|---|---|
| 5 | CHO | $-O-C_6H_{13}$-n | B.p. 110–115° C./0.07 mbar |
| 6 | CHO | $-O-C_8H_{17}$-n | B.p. 110–115° C./0.2 mbar |
| 7 | CHO | $-OC_3H_7$-n | Oil |
| 8 | CHO | $-OC_4H_9$-n | Oil |
| 9 | CHO | $-OC_4H_9$-iso | Oil |
| 10 | CHO | $-OC_5H_{11}$-n | Oil |
| 11 | CHO | $-OC_{10}H_{21}$ | B.p. 110–120° C./0.02 mbar |
| 12 | CHO | $-O-CH_2-C(CH_3)_3$ | Oil |
| 13 | CHO | $-O-CH_2-CH(C_2H_5)_2$ | B.p. 102–105° C./0.05 mbar |
| 14 | CHO | $-NH-CH_3$ | M.p. 125–128° C. |
| 15 | CHO | $-O-CH_2-CH_2-CH(CH_3)_2$ | B.p. 80–90° C./0.4 mbar |
| 16 | CHO | $-O-C_2H_4-\text{C}_6H_5$ | B.p. 80–100° C./0.03 mbar |
| 17 | CHO | $-O-CH_2-CH(C_2H_5)-CH_2-CH_2-CH_2-CH_3$ | B.p. Kp. 90–100° C./0.1 mbar |
| 18 | CHO | $-O-C_2H_4-OCH_3$ | B.p. 80–86° C./0.1 mbar |

USE EXAMPLES

In the use examples which follow, the compound listed below was employed as a comparative substance:

1-Amino-cyclopropane-1-carboxylic acid hydrochloride (disclosed in EP-OS (European Published Specification) 5,782)

EXAMPLE A

Inhibition of growth of summer barley

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amount of solvent and emulsifier and the mixture is made up to the desired concentration with water.

Summer barley plants are grown in a greenhouse until the last leaf has appeared. In this stage, the plants are sprayed with the preparations of active compound until dripping wet. After 3 weeks, the additional growth is measured on all plants and the inhibition of growth in per cent of the additional growth of the control plants is calculated. 100% inhibition of growth means that growth has stopped and 0% denotes a growth corresponding to that of the control plants.

In this test, the compound according to example (1) shows a substantially better activity than the comparative substance (A).

EXAMPLE B

Inhibition of growth of summer wheat

Solvent: 30 parts by weight of dimethylformamide
Emulsifier: 1 part by weight of polyoxyethylene sorbitane monolaurate To produce a suitable preparation of active compound, 1 part by weight of active compound is mixed with the stated amounts of solvent and emulsifier and the mixture is made up to the desired concentration with water.

Summer wheat plants are grown in a greenhouse until the last leaf has appeared. In this stage, the plants are sprayed with the preparations of active compound until dripping wet. After 3 weeks, the additional growth is measured on all plants and the inhibition of growth in per cent of the additional growth of the control plants is calculated. 100% inhibition of growth means that growth has stopped and 0% denotes a growth corresponding to that of the control plants.

In this test, the compound according to example (1) shows a substantially better activity than the comparative substance (A).

EXAMPLE C

Stimulation of the fixation of $CO_2$ in soya beans

Solvent: 30 parts by weight of dimethylformamide
Emulsifier: 1 part by weight of polyoxyethylene sorbitane monolaurate To produce a suitable preparation of active compound, 1 part by weight of active compound is mixed with the stated amounts of solvent and emulsifier and the mixture is made up to the desired concentration with water.

Soya bean plants are grown in a greenhouse until the first secondary leaf has unfolded completely. At this stage, the plants are sprayed with the preparations of active compound until dripping wet. In the further course of the experiment, the fixation of $CO_2$ in the plants is determined by customary methods. The values are compared with those of the control plants, which have not been treated with the active compounds.

The figures of merit have the following meanings:

— denotes inhibition of the fixation of $CO_2$
O denotes fixation of $CO_2$ as in the case of the control
+ denotes low stimulation of the fixation of $CO_2$
++ denotes powerful stimulation of the fixation of $CO_2$
+++ denotes very powerful stimulation of the fixation of $CO_2$ In this test, the compounds according to examples (1) and (2) show a substantially better activity than the comparative substance (A).

We claim:

1. A 1-methylamino-cyclopropane-1-carboxylic acid derivative of the formula

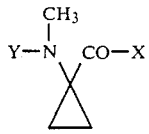

in which
X is hydroxyl, and
Y is hydrogen
or a hydrochloric acid addition salt thereof.

2. A 1-methylamino-cyclopropane-1-carboxylic acid derivative of the formula

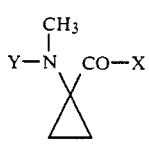

in which
X is methoxy,
Y is hydrogen
or a hydrochloric acid addition salt thereof.

* * * * *